United States Patent [19]
Mallory et al.

[11] Patent Number: 5,260,668
[45] Date of Patent: Nov. 9, 1993

[54] SEMICONDUCTOR SURFACE RESISTIVITY PROBE WITH SEMICONDUCTOR TEMPERATURE CONTROL

[75] Inventors: Chester L. Mallory, Campbell; Walter H. Johnson; Wayne K. Borglum, both of San Jose, all of Calif.

[73] Assignee: Prometrix Corporation, Santa Clara, Calif.

[21] Appl. No.: 897,459

[22] Filed: Jun. 11, 1992

[51] Int. Cl.$^5$ .................. G01R 27/08; G01N 27/14
[52] U.S. Cl. ................... 324/719; 324/158 R; 324/703; 324/715
[58] Field of Search ............ 324/691, 693, 702, 703, 324/715, 716, 719, 721, 158 R; 165/80.5, 80.4

[56] References Cited

U.S. PATENT DOCUMENTS

| | | | |
|---|---|---|---|
| 3,842,346 | 10/1974 | Bobbitt | 324/537 X |
| 3,890,567 | 6/1975 | Knufflmann et al. | 324/64 |
| 4,226,693 | 10/1980 | Maes | 204/195 |
| 4,383,217 | 5/1983 | Shiell | 324/158 F |
| 4,420,974 | 12/1983 | Lord | 73/154 |
| 4,532,797 | 8/1985 | Yang | 73/75 |
| 4,706,015 | 11/1987 | Chen | 324/64 |
| 4,739,258 | 4/1988 | Schwarz | 324/703 X |
| 4,755,746 | 7/1988 | Mallory et al. | 324/158 F |
| 4,888,818 | 12/1989 | Schmitt et al. | 324/439 |
| 4,888,987 | 12/1989 | Zhang | 73/204.14 |
| 4,989,154 | 1/1991 | Yamashita et al. | 324/719 X |

*Primary Examiner*—Gerard R. Strecker
*Assistant Examiner*—Diep Do
*Attorney, Agent, or Firm*—Townsend and Townsend Khourie and Crew

[57] ABSTRACT

The resistivity of the surface of a semiconductor wafer is measured at different temperatures to determine the resistivity as a function of temperature. The temperature of the semiconductor wafer is varied by a heater in thermal contact with the semiconductor wafer, and the temperature is measured by a temperature sensor in thermal contact with the semiconductor. The heater is controlled by a control unit which adjusts the amount of heat provided by the heater, thereby controlling the temperature at which a measurement from a four-point resistivity probe is taken.

9 Claims, 3 Drawing Sheets

SEMICONDUCTOR SURFACE RESISTIVITY PROBE WITH SEMICONDUCTOR TEMPERATURE CONTROL

BACKGROUND OF THE INVENTION

The present invention relates to the field of resistivity measurement of semiconductor surfaces.

In the prior art, the variation of resistivity as a function of temperature in semiconductors was either ignored or a particular value for the thermal coefficient of resistivity was assumed. The thermal coefficient of resistivity, or the ratio of the change in resistivity over a 1° C. temperature change, is small for bulk silicon or unprocessed silicon wafers. Typical values are ±1%/° C., i.e. the resistivity of the wafer surface varies up to 1 percent over a 1° C. variation of the temperature at the wafer surface. Since a 1% variation is such a small change, the thermal coefficient of resistivity is often ignored. Ignoring the coefficient is equivalent to using a value of 0%/° C. for the thermal coefficient of resistivity, resulting in an error in a resistivity reading of about ±1% for each 1° C. of thermal drift during the measurement process. In many applications, such an error might be insignificant, however as the demands placed on semiconductors for ever smaller and faster circuits, such errors become very problematic.

Where the thermal coefficient of resistivity is not ignored, a value for the coefficient is often selected from a table of coefficients for silicon wafers having various dopant concentrations. While this may result in suitable coefficient approximations for unprocessed silicon, the thermal coefficient of resistivity for a patterned thin film layer on the surface of a wafer cannot be easily determined by reference to a table. Furthermore, this would yield only a crude approximation, since many more characteristics of a wafer affect the value of the coefficient than can be accounted for in any table of a reasonable size. Thus, in many other applications where the thermal coefficient of resistivity is not ignored, the accuracy of a table coefficient is sufficient. Nonetheless, some applications require even more accuracy.

Semiconductor wafers with high dopant concentrations will have lower resistivities, so in terms of absolute resistivity, a percentage error in a resistivity measurement causes a small error in the absolute resistivity, and a resistivity measurement ignoring the thermal variation might be in error by only a small percentage. However, as resistivity increases, the absolute error increases, as for example, when the dopant concentration is lowered. When two high resistivity areas of the wafer must be matched, as in analog resistor pair matching, the absolute error is more important than the percentage variation. For example, on a wafer with two matched areas of approximately 50 MΩ/square, ignoring the thermal coefficient of resistivity can result in an error of as much as 50 KΩ/square in the differential resistivity between the areas.

From the above it is seen that an improved method and apparatus for measuring resistivity to account for the thermal coefficient of resistivity are needed.

SUMMARY OF THE INVENTION

The resistivity of the surface of a semiconductor wafer is measured at different temperatures to determine the resistivity as a function of temperature. The temperature of the semiconductor wafer is varied by a heater in thermal contact with the semiconductor wafer, and the temperature is measured by a temperature sensor in thermal contact with the semiconductor. The heater is controlled by a control unit which adjusts the amount of heat provided by the heater, thereby controlling the temperature at which a measurement from a four-point resistivity probe is taken.

In another embodiment of the present invention, the heater and sensor can be used to fix the temperature of the wafer at one value, to allow multiple resistivity measurements at the fixed temperature.

A further understanding of the nature and advantages of the inventions herein may be realized by reference to the remaining portions of the specification and the attached drawings.

DESCRIPTION OF THE PREFERRED EMBODIMENTS

Figure 1:
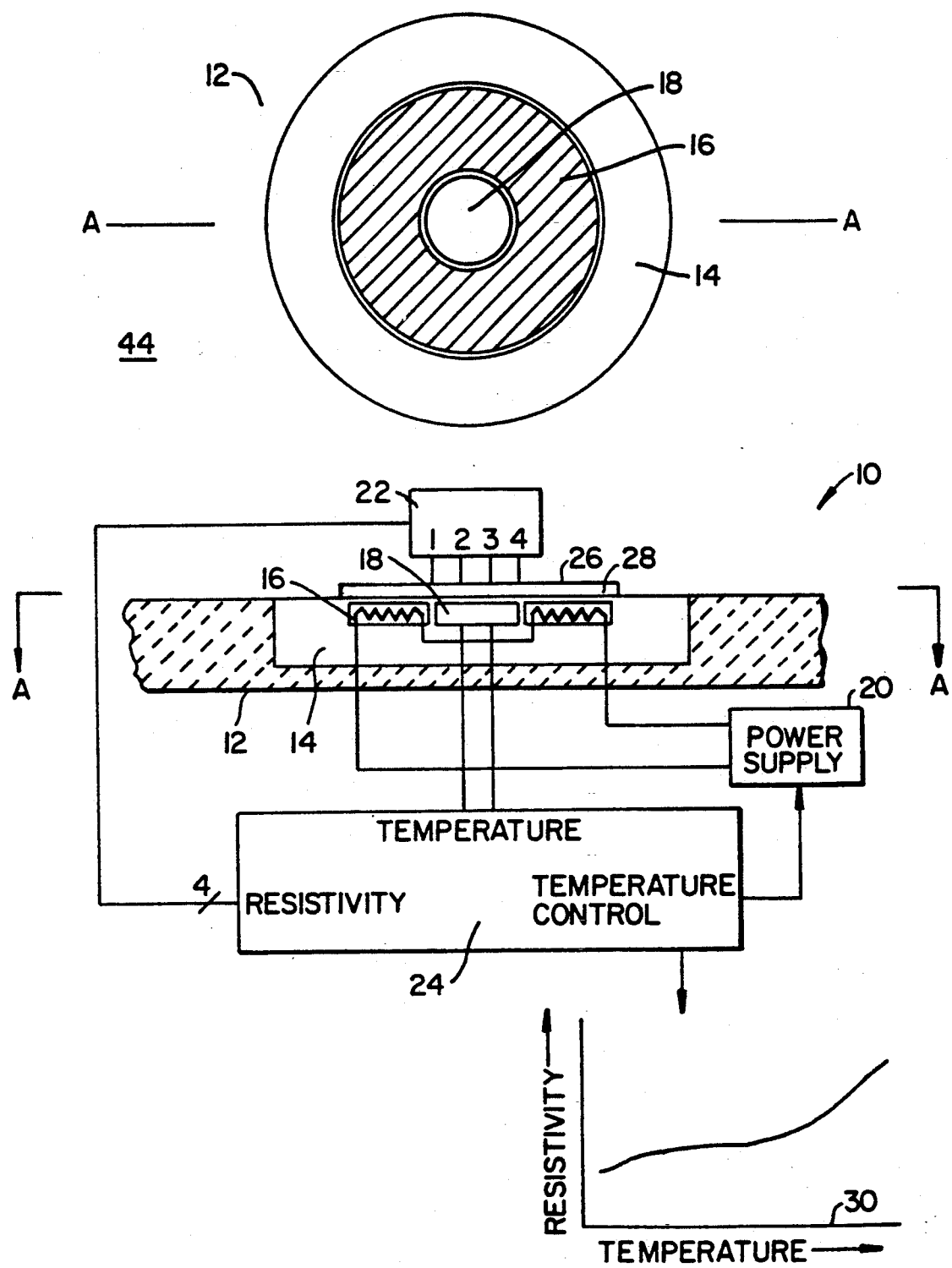
FIG. 1 illustrates a particular embodiment of a resistivity measurement device according to the present invention.

Referring to FIG. 1, a resistivity apparatus 10 according to the present invention includes a mount 12, a heat block 14, a heater 16, a sensor 18, a power supply 20, a four-point probe 22, and a control unit 24. Resistivity apparatus 10 measures the resistivity of a surface 26 of a semiconductor wafer 28 to produce data shown in graphical form as graph 30.

Because of the thickness and thermal conductivity of semiconductor wafer 28 and its proximity to sensor 18, the temperature at sensor 18 is essentially the temperature of wafer 28 at surface 26. Control unit 24 controls the amount of power supplied by power supply 20 to heater 16, thus effectively controlling the heat supplied to wafer 28. The heat from heater 16 only heats heat block 14 and not mount 12, because heat block 14 is insulated from mount 12, allowing fine control of the heat supplied to wafer 28.

In one embodiment of the present invention, wafer 28 is at the nominal temperature for which a resistivity measurement is to be taken, and wafer 28 is heated up to the highest temperature for which a measurement is to be taken. A number of resistivity measurements are taken during the period of heating, or the resistivity is continuously recorded. In another embodiment, wafer 28 can be cooled as well as heated, to allow for more precise temperature control. The precise temperature control is due to the fact that the wafer can be cooled if it is hotter than a temperature for which a measurement is to be taken. If wafer 28 can only be heated but not cooled, measurements at a predetermined temperature cannot be made once the wafer is hotter than that temperature. In most practical applications, a cooling means is provided, however it is not necessary in all embodiments.

In various other embodiments of the present invention, wafer 28 or heat block 14 is cooled through thermal contact with a relatively cold mount 12 which drains heat from wafer 28, or wafer 28 is exposed to a relatively cold atmosphere of air or nitrogen 44.

If the measurement of resistivity versus temperature must be done in a short time period, heat is continuously applied to heat block 14 and the resistivity versus temperature function is measured in a single pass from a cold wafer to a hot wafer. However, if more time is available for measurement, control unit 24 selects a first temperature, controls the heat supplied to wafer 28 until the temperature of wafer 28 is stabilized at the first temperature, measures the resistivity of surface 26, and then controls the heat supplied to wafer 28 to reach a second temperature, and so on, for as many temperature points as needed for a useful graph.

Figure 2:
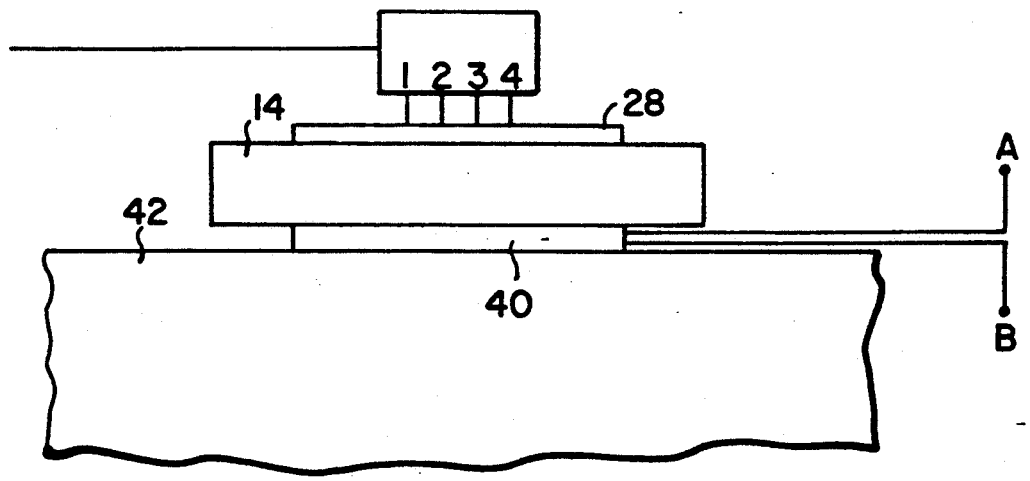
FIG. 2 illustrates a heating unit of an alternative embodiment using a thermoelectric device to heat and cool a semiconductor wafer.

FIG. 2 illustrates an alternative embodiment of the present invention. A thermoelectric plate 4 is used to heat and cool wafer 28. With a thermoelectric plate, the direction of heat flow is determined by the direction of current flow through the plate. In FIG. 2, for example, if a current is caused to flow from terminal A to terminal B, heat flows from heat block 14 to a heat sink 42, and wafer 28 is cooled as wafer 28 replaces the heat drawn out of heat block 14. On the other hand, if the current is caused to flow from terminal B to terminal A, heat flows from heat sink 42 to heat block 14, and wafer 28 is heated by the heat added to heat block 14. If necessary, heat sink 42 can be made massive enough so that heat transferred to and from heat sink 42 through thermoelectric plate 40 does not significantly change the temperature of heat sink 42.

Of course, the temperature at the wafer need not be varied for resistivity measurement device 10 to be useful over the prior art. For fixed temperature measurements, control unit 24 adjusts the heat from heater 16 to ensure a constant temperature at heat block 14 using sensor 18 to detect temperature drifts, thereby keeping the temperature of wafer 28 constant. While the temperature is held constant by the action of control unit 24, sensor 18 and heater 16, four-point probe 22 can be moved to different locations on surface 26, to measure resistivity at those different locations. One application of a fixed temperature resistivity measuring device is for comparing the resistivity of two or more areas on a wafer, where the difference must be measured very accurately and where thermal drifts would cause undesirable measurement errors.

In another embodiment of the present invention, the temperature is not controlled, but is merely recorded. In that embodiment a means for heating/cooling the wafer is not needed. Such a system is useful for making measurements where the relationship between resistivity and temperature is known, especially where resistivity measurements must be taken in less time than a wafer temperature stabilization time.

According to one aspect of the invention, the heater and temperature sensor are less than 30 mil thick, with the temperature sensor and the heater being coplanar, and with each having a low thermal mass. In a specific embodiment of the present invention, the heater is an etched metal film heater, of platinum, nickel/iron, indium-tin-oxide, nickel, or copper, and the temperature sensor is either an etched metal element or a wire wound element comprising a suitable material with a high temperature coefficient of resistance. In other embodiments of the invention, the temperature sensor is a thermocouple, thermistor, or lattice vibration sensor. In still other embodiments, temperature is measured using an optical sensor, which typically measures infra-red radiation radiating from the surface of a semiconductor.

Figure 3:
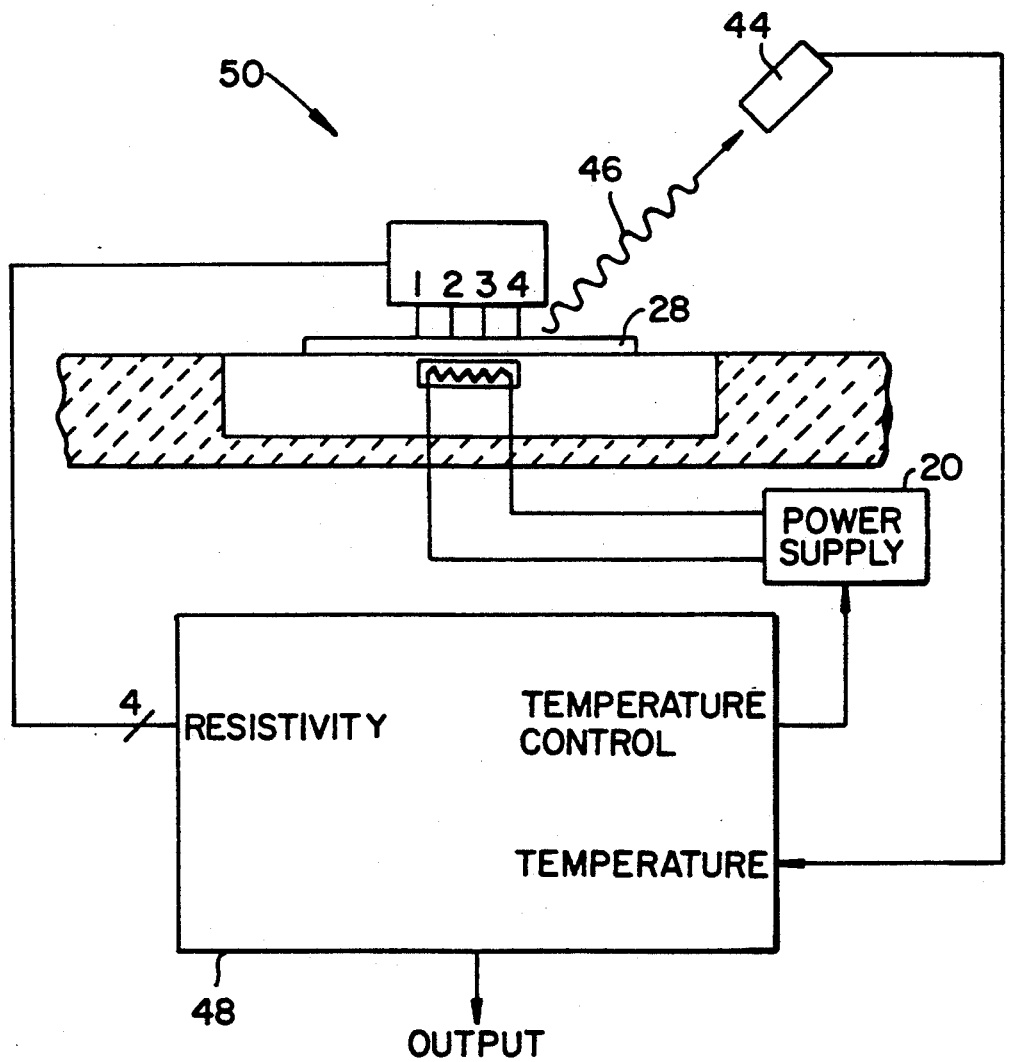
FIG. 3 illustrates a particular embodiment of a resistivity measurement device wherein an optical sensor is used to measure temperature.

FIG. 3 shows a resistivity measurement device 50, similar to resistivity measurement device 10 shown in FIG. 1, with an optical temperature sensor 44. Instead of physical contact between a temperature sensor and a semiconductor wafer 28, optical temperature sensor 44 is used to measure the infra-red radiation 46 emitted by semiconductor wafer 28. The temperature measured by optical temperature sensor 44 is input to control unit 48, which regulates the output of power supply 20 accordingly.

Figure 4:
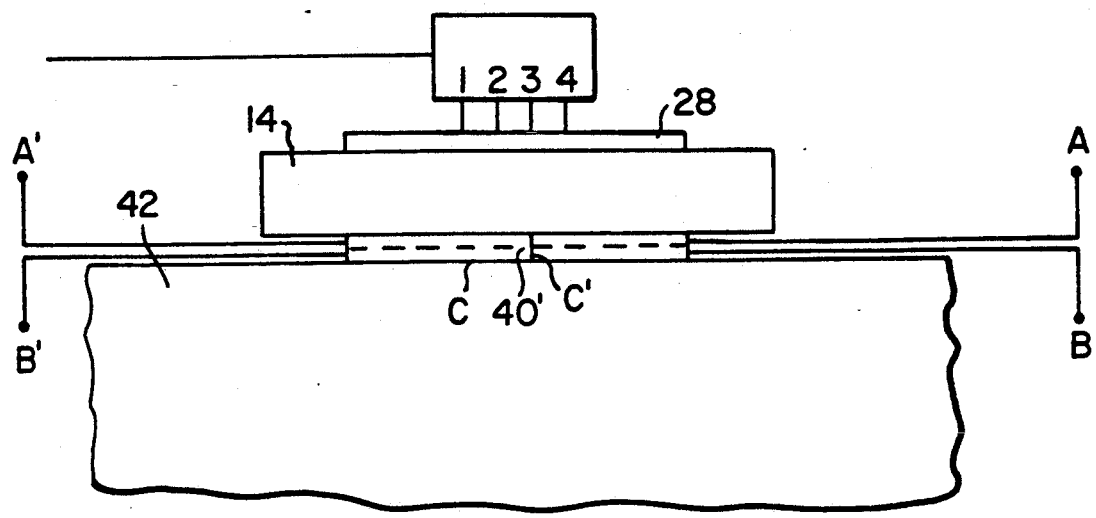
FIG. 4 illustrates an alternate embodiment using separate heating and cooling means to adjust the temperature of a semiconductor wafer.

FIG. 4 illustrates a variation of thermoelectric plate 40. A thermoelectric plate 40'shown in FIG. 4, comprises separate heating and cooling plates, each with separate controls, A13 B and A'-B'. the separate plates can be positioned vertical to each other as indicated by line C, or horizontal to each other as indicated by line C'. Alternately, cooling atmosphere 44 could be used as a cooling means.

The above description is illustrative and not restrictive. Many variations of the invention will become apparent to those of skill in the art upon review of this disclosure. Merely by way of example, radiant heaters could be used to heat wafer 28, and wafer 28 could be cooled by radiant heat dissipation. In another embodiment, instead of a circular sensor and an annular heater, the sensor and the heater are interlocking spirals around a common center. The scope of the invention should, therefore, be determined not with reference to the above description, but instead should be determined with reference to the appended claims along with their full scope of equivalents.

What is claimed is:

1. An apparatus for measuring the resistivity of a surface of a semiconductor wafer as a function of temperature of the surface, comprising:

a heat transfer means thermally coupled to the semiconductor wafer for transferring heat to the semiconductor wafer, said heat transferred to the semiconductor wafer at a rate determined by a heat transfer signal input to said heat transfer means;

a temperature sensor thermally coupled to the semiconductor wafer, said temperature sensor outputting a temperature signal indicating a temperature of the surface;

a four-point resistivity probe electrically coupled to the surface of the semiconductor wafer, said four-point probe outputting a resistivity signal indicating the resistivity of the surface; and a signal processing means, coupled to receive said resistivity signal and said temperature signal, and coupled to output said heat transfer signal to said heat transfer means, for adjusting said heat transfer signal until said temperature signal indicates the surface of the semiconductor wafer is at a desired temperature, said signal processing means also for outputting a resistivity value corresponding to said resistivity signal when said temperature signal indicates that the surface of the semiconductor wafer is at said desired temperature.

2. The apparatus of claim 1, wherein said desired temperature is a constant value for a period of time, and wherein said four-point resistivity probe is placed in contact with a plurality of locations on the surface during said period of time, thereby allowing said signal processing means to serially measure a resistivity value of the surface using said four-point probe at each of said plurality of locations during said period of time when said desired temperature is constant.

3. The apparatus of claim 1, wherein said signal processing means causes said heat transfer means to transfer heat away from the semiconductor wafer when said temperature signal indicates that the semiconductor wafer is hotter than said desired temperature.

4. The apparatus of claim 1, wherein said heat transfer means comprises a single thermoelectric unit capable of transferring heat to and from the semiconductor wafer.

5. A method of measuring resistivity as a function of temperature on the surface of a semiconductor wafer, comprising the steps of:
   mounting a temperature sensor in thermal contact with the semiconductor wafer;
   applying the contacts of a four-point resistivity probe to the surface of the semiconductor wafer;
   transferring heat between said semiconductor wafer and a surrounding environment to cause a temperature measured by aid temperature sensor to vary over a desired temperature range; and
   measuring, at a plurality of measured temperatures within said desired temperature range, a resistivity value using said four-point resistivity probe.

6. The method of claim 5, further including the steps of:
   placing the semiconductor wafer in thermal contact with a heating means and a cooling means;
   applying less heat with said heating means to the semiconductor wafer than is drawn from the semiconductor wafer by said cooling means when said resistivity value to be measured in said measuring step is to be measured at a temperature lower than the temperature measured by said temperature sensor; and
   applying more heat with said heating means to the semiconductor wafer than is drawn from the semiconductor wafer by said cooling means when said resistivity value to be measured in said measuring step is to be measured at a temperature higher than the temperature measured by said temperature sensor.

7. The method of claim 6, wherein said step of placing the semiconductor wafer in thermal contact with said cooling means comprises the step of placing the semiconductor wafer in thermal contact with an atmosphere surrounding the semiconductor wafer.

8. A method for measuring resistivity as a function of temperature on the surface of a semiconductor wafer, comprising the steps of:
   coupling the semiconductor wafer to a heat transfer means, wherein said heat transfer means changes a temperature of the semiconductor wafer by transferring heat between the semiconductor wafer and a surrounding environment;
   mounting a temperature sensor in thermal contact with the semiconductor wafer;
   applying the contacts of a four-point resistivity probe to the surface of the semiconductor wafer;
   holding the semiconductor wafer at a fixed temperature, using said heat transfer means and said temperature sensor; and
   measuring, at said fixed temperature, a resistivity value using said four-point resistivity probe.

9. An apparatus for measuring the resistivity of a surface of a semiconductor wafer as a function of temperature of the surface, comprising:
   a heat transfer means adapted to transfer heat between said heat transfer means and a semiconductor wafer, said heat transfer means thermally coupled to said semiconductor wafer when said semiconductor wafer is under test, said heat transferred to said semiconductor wafer at a rate determined by a heat transfer signal input to said heat transfer means;
   a temperature sensor adapted to sense a temperature of said semiconductor wafer, said temperature sensor thermally coupled to said semiconductor wafer when said semiconductor wafer is under test, wherein said temperature sensor outputs a temperature signal indicating said temperature of the surface of said semiconductor wafer;
   a four-point resistivity probe adapted to supply a test current to said semiconductor wafer and adapted to measure a voltage on said surface of said semiconductor wafer, said four-point resistivity probe electrically coupled to said surface of said semiconductor wafer when said semiconductor wafer is under test, said four-point resistivity probe outputting a resistivity signal indicating a resistivity value of said semiconductor wafer when said semiconductor wafer is under test; and
   a signal processing means, coupled to receive said resistivity signal and said temperature signal, coupled to supply said test current, and coupled to output said heat transfer signal to said heat transfer means, for adjusting said heat transfer signal until said temperature signal indicates a desired temperature, said signal processing means also for outputting a resistivity value corresponding to said resistivity signal when said temperature signal indicates said desired temperature.

* * * * *